(12) United States Patent
Sundaresan et al.

(10) Patent No.: US 8,602,034 B2
(45) Date of Patent: Dec. 10, 2013

(54) MAGNETOELECTRIC SURGICAL TOOLS FOR MINIMALLY INVASIVE SURGERY

(75) Inventors: Vishnu-Baba Sundaresan, Richmond, VA (US); Jayasimha Atulasimha, Glen Allen, VA (US); Joshua Clarke, Mechanicsville, VA (US)

(73) Assignee: Virginia Commonwealth University, Richmond, VA (US)

( * ) Notice: Subject to any disclaimer, the term of this patent is extended or adjusted under 35 U.S.C. 154(b) by 521 days.

(21) Appl. No.: 12/889,857

(22) Filed: Sep. 24, 2010

(65) Prior Publication Data

US 2011/0077663 A1    Mar. 31, 2011

Related U.S. Application Data

(60) Provisional application No. 61/245,793, filed on Sep. 25, 2009.

(51) Int. Cl.
  *A61B 19/00*    (2006.01)
(52) U.S. Cl.
  USPC .......................................................... 128/899
(58) Field of Classification Search
  USPC ........................................ 600/9–15; 606/130
  See application file for complete search history.

(56) References Cited

U.S. PATENT DOCUMENTS

| | | | | |
|---|---|---|---|---|
| 4,443,731 | A * | 4/1984 | Butler et al. | 310/334 |
| 6,015,386 | A * | 1/2000 | Kensey et al. | 600/486 |
| 2003/0193399 | A1* | 10/2003 | Hum et al. | 340/573.4 |
| 2004/0068173 | A1* | 4/2004 | Viswanathan | 600/407 |
| 2006/0145831 | A1* | 7/2006 | Bornhoevd et al. | 340/521 |
| 2007/0285244 | A1* | 12/2007 | Tucker et al. | 340/572.1 |
| 2008/0297340 | A1 | 12/2008 | Popa et al. | |

* cited by examiner

*Primary Examiner* — Christine Matthews
*Assistant Examiner* — Joshua D Lannu
(74) *Attorney, Agent, or Firm* — Whitham Curtis Christofferson & Cook, PC

(57) ABSTRACT

A magnetoelectric element of a surgical tool positioned in the body of a subject is controllably bent or elongated under the influence of an applied magnetic field. A piezoelectric layer in the magnetoelectric element provides output that can be used to determine the actual amount of bending or elongation of the magnetoelectric element, and this actual amount is compared to a theoretical amount of bending or elongation which would result from the applied magnetic field. Any differences between the actual and theoretical amounts provide feedback to the surgeon for performing the surgical procedure. Preferably, tactile feedback is provided to the surgeon.

11 Claims, 8 Drawing Sheets

(a) Concept schematic for the magnetoelectric surgical tool (a) Concept schematic for the
magnetoelectric surgical tool (b) Application in artery with plaque -
(Electromagnets placed outside the patient)

MAGNETOELECTRIC SURGICAL TOOLS FOR MINIMALLY INVASIVE SURGERY

CROSS-REFERENCE TO RELATED APPLICATIONS

This application claims priority to U.S. Provisional Patent Application 61/245,793 filed on Sep. 25, 2009, and the complete contents thereof is herein incorporated by reference.

BACKGROUND OF THE INVENTION

1. Field of the Invention

The present invention generally relates to surgical tools and systems which will be controlled by a computer but which will provide feedback to the surgeon.

2. Background Description

Minimally invasive surgery generally describes a process for conducting surgical procedures such as cutting, scraping, activating, etc. inside the body of a subject without having to open an area in the subject to allow the surgeon access to a site or location. Examples of minimally invasive surgery include any endoscopic device with an actuator, i.e., an instrument which is deployed into a body canal, organ, etc., which enables, for example, visual observation on a display of the area around the endoscopic device (some tools do not utilize visual imaging) and which allows selective control of an actuatable device extending from the endoscopic tool. For example, balloon catheters are used in heart surgery under the control of the surgeon that views the position of the catheter inside an artery on a display. The surgeon can selectively actuate a balloon inside the artery at a desired location. A variety of other actions can also be taken such as deployment of a stent, administration of pharmaceuticals at a desired location, etc.

One of the requirements for minimally invasive surgery is that the instruments that are deployed be quite small. Mechanical cutting tools have been miniaturized for these types of surgeries, but suffer from a necessary bulk required for mechanical linkages and other actuation mechanisms. Piezoelectric materials, shape memory alloys, and ionic polymer actuators have also been employed. For example, piezoelectric ultrasonic generators have been used in endodontics, periodontology, bone osteomy, and maxillofacial surgery. Piezoelectric bimorphs have also been used to function as grippers and sensors in robotic surgical devices. Thin film piezoelectric patches have been used on angioplasty balloons for measuring the thickness of arterial plaque. Smart memory alloys such as Nitinol have been used in self-expanding heart stents and in implantable heart valves. Shape memory alloys are also being developed for applications as replacement tissues and filters. Ionic polymer actuators have been suggested for use in fixation devices and in surgical stapling applications.

While there have been many advances allowing for the use of computer controlled actuators, surgery still requires the sound judgment of a skilled surgeon. For example, he or she will need the ability to make fine and precise cuts without damaging other tissues, organs, nerves, etc. in the regions where the cuts are made. A distinct impediment to the advancement of minimally invasive surgery is the ability to provide the surgeon with feedback that allows the surgeon to know exactly what is going on at the surgical site.

SUMMARY OP THE INVENTION

An embodiment of the invention provides a magnetostrictive material actuatable by externally applied magnetic forces, together with a piezoelectric material that provides feedback on the operations performed by the magnetostrictive material (e.g., expansion, bending, etc.), and where a comparison of the feedback information from the piezoelectric material with the theoretically achievable operations (e.g., expansion, bending, etc.) provides feedback to the surgeon.

According to the invention, a surgical tool includes a multilayer portion which includes at least one magnetostrictive layer and at least one piezoelectric layer. Other layers made out of silicon, epoxy, polyimide etc., may also be included. The surgical tool can perform an operation, such as extension or bending, under the influence of an externally applied magnetic field. The piezoelectric layer acts as a sensor to provide feedback on the performed operation. Differences between the theoretical operation of the multilayer portion (e.g., the amount of extension or bending which might be expected based on the applied magnetic field) and the actual operation (as determined by output from the one or more piezoelectric layers) will be determined and these difference measures will be used to provide feedback to the surgeon. The feedback can be in the form of visual and/or tactile feedback (in a preferred embodiment, tactile feedback is provided). In this way, the surgeon can determine a number Of things not previously available to him or her from computer controlled systems. For example, he or she will be able to determine, for example, the degree of difficulty in cutting a tissue, the degree of difficulty in scraping an artery wall, etc. If the theoretical and actual measurements are different (e.g., Off by 5%, 10%, 25% or more) the surgeon will know that the tissue being cut or scraped is "tough", "fibrous", "elastic", or some other property which would tell the surgeon to keep applying the magnetic field and/or to oscillate the magnetic field or take some other action so that the tissue can be effectively cut or scraped in a safe and precise manner. In contrast, if the theoretical and actual measurements are approximately the same, the surgeon can better determine when to stop applying the magnetic field (e.g., most of the restenosis material has been scraped from an artery, etc.). This type of feedback will help the surgeon determine when to stop a particular procedure, and will allow for more precise control over the procedure. This type of feedback can be used in conjunction with visual feedback or without visual feedback.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION

Figure 1A:
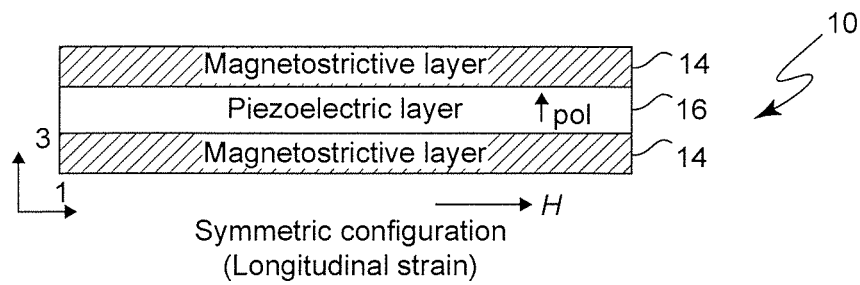
FIGS. 1a and 1b show exemplary multilayer magnetoelectric structures for respectively elongating and bending under the influence of an applied magnetic field.
Figure 1B:
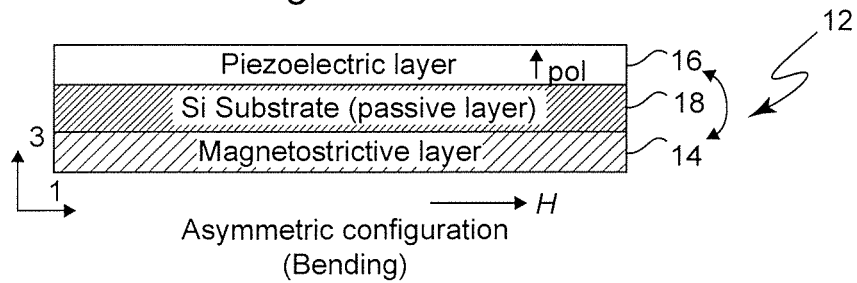

Referring now to the drawings, FIGS. 1a and 1b respectively show examples of multilayer magnetoelectric elements 10 and 12 which may be used in the practice of the present invention. The magnetoelectric element 10 in FIG. 1a includes two magnetostrictive layers 14 on opposite sides of a piezoelectric layer 16. The magnetoelectric element 10 will expand and contract in the longitudinal direction when subjected to an applied magnetic field H. The magnetoelectric element 12 in FIG. 1b includes a magnetostrictive layer 14 and a piezoelectric layer 16 on opposite sides of a substrate 18, e.g., a passive layer such as a Si based or Ge based substrate (e.g., Si, silicon dioxide, Ge, or Ge alloys) and constrained to move at one end. The magnetoelectric element 12 will bend when subjected to an applied magnetic field H.

Either configuration of the magnetoelectric element 10 or 12 can be useful for performing a variety of surgical procedures. The number of layers of each type of material can vary widely depending on the application with the only requirement being that the magnetoelectric element 10 or 12 have at least one magnetostrictive layer 14 for performing an operation under an applied magnetic field (e.g., bending or elongating) and at least one piezoelectric layer 16 for providing a sensing function to sense the operation which has been performed (e.g., degree of actual bending or elongation).

The choice of material for the magnetostrictive layer 14 can vary considerably. Exemplary magnetostrictive materials include Galfenol (Iron Gallium), Terfenol-D (Terbium Dysprosium Iron), Cobalt Ferrite, Nickel Ferrite, Lithium Ferrite, Yttrium Iron Garnet, Copper Ferrite, Manganese Ferrite, $LaCaMnO_3$, $LaSrMnO_3$, $SmFe_2$, $TbFe_2$, Permendur (Iron Cobalt. Vanadium), Ni2MnGa, Nickel, and Metglas. The choice of material for the piezoelectric layer 16 can vary considerably. Exemplary piezoelectric layers include Lead Zirconate Titanate, Lead Magnesium Niobate-Lead Titanate, Polyvinylidine Fluoride, and Lead Zirconium Niobate-Lead Titanate.

Figure 2:
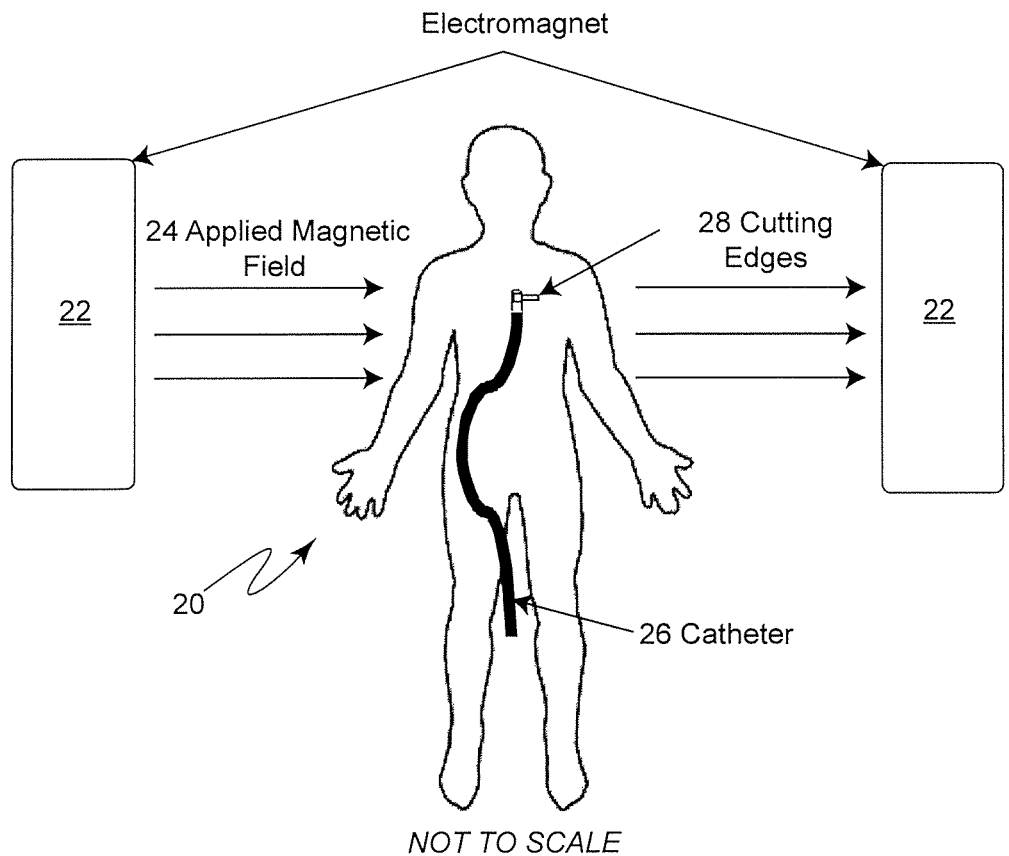
FIG. 2 shows a schematic of an exemplary cutting or scraping device being used in a subject.

FIG. 2 shows a subject 20 (human or animal or a non-living material) positioned between magnets 22 that create a strong applied magnetic field 24. The magnets 22 can be permanent magnets or electromagnets and in a preferred arrangement they include a Helmholtz Coil. In the exemplary embodiment shown in FIG. 2, a catheter 26 is directed through a human subject's 20 veins to his heart, and a cutting tool 28 is projected from the catheter 26 at a site where cutting or scraping is to be performed (e.g., an artery wall, tumor removal, endoscopy, etc.,).

Figure 3A:
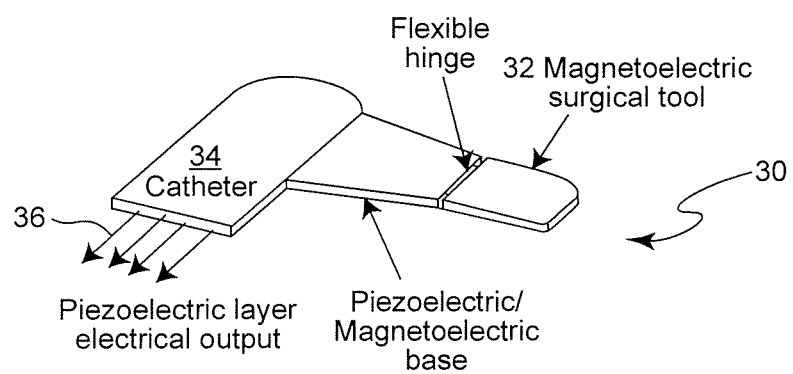
FIGS. 3a and 3b show schematics of an exemplary cutting or scraping device used in the artery to remove plaque.

FIG. 3a shows an exploded view of an exemplary catheter deployed scraping device 30. The device 30 includes a surgical tool 32 of which at least a portion is a multilayered magnetoelectric element such as depicted in FIGS. 1a and 1b. The surgical tool 32 projects out of an Opening (not shown) in a catheter 34. Retention of the surgical tool 32 in the catheter 34 and selective deployment of the surgical tool 32 can be accomplished by a variety of techniques. FIG. 3a shows that output 36 from the piezoelectric layer in the surgical tool 32 can be directed, for example, using wired connections that traverse the catheter 34. However, in some applications a transmitter (not shown) might be included in the catheter 34 to transmit by wireless communication output 36 sensed from the piezoelectric layer in the surgical tool 32. The design shown in FIG. 3a has the surgical tool 32 mounted on a piezoelectric/magnetic base 38. This allows for elongation of the base 38 as well as, for example, bending of the surgical tool 32.

Figure 3B:
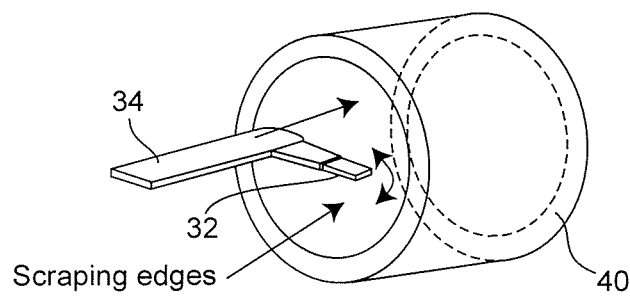

FIG. 3b shows the catheter 34 and surgical tool 32 within an artery 40 for removing plaques formed therein as is indicated by the double headed arrow. In this application, scraping edges might be formed on or affixed to the multilayer magnetoelectric element of the surgical tool 32. Alternatively, the scraping members might extend from the magnetoelectric portion of the surgical tool.

Figure 4A:
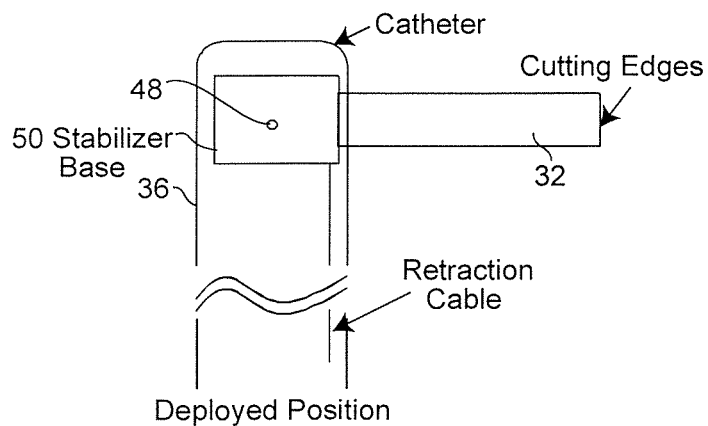
FIGS. 4a-c show schematics of an exemplary cutting or scraping device which can be deployed from a catheter.
Figure 4B:
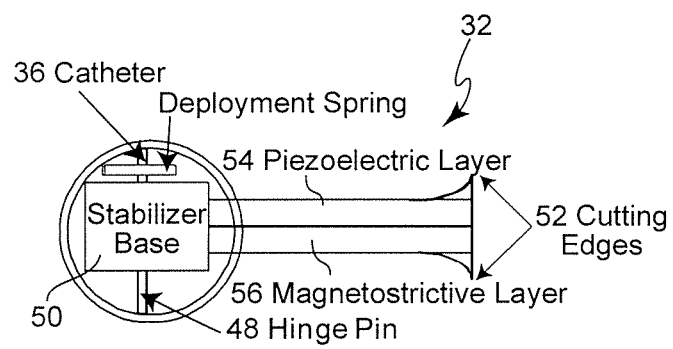
Figure 4C:
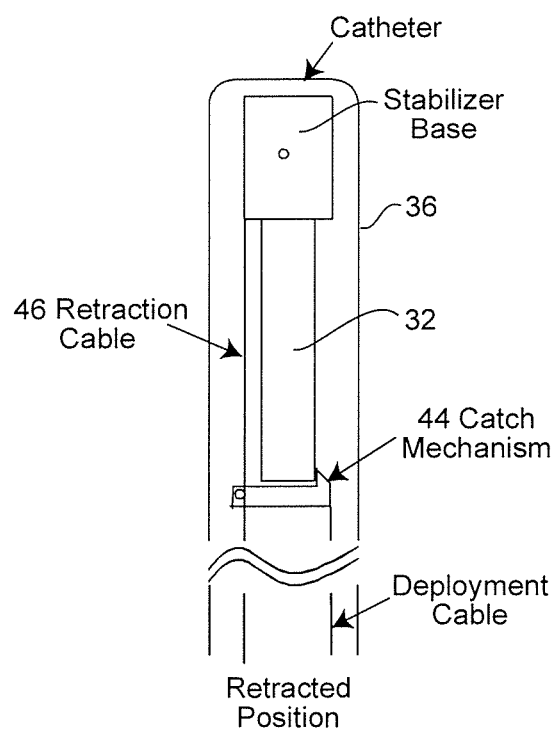

FIGS. 4a-c show one example for selectively deployed the surgical tool 32 shown in FIGS. 3a-b, it being understood by those of skill in the art that a variety of other techniques may be practiced within the scope of the invention. FIG. 4a shows the surgical tool 32 extending from the catheter 36 in the "deployed position" while FIG. 4c shows the surgical tool 32 within the catheter 36 in the "retracted position". FIG. 4c shows a deployment cable 42 for mechanically operating a catch mechanism 44 to allow the surgical tool 32 to be deployed from the catheter 35. In the "retracted position" the catch mechanism 44 secures the surgical tool 32 within the catheter 36. FIG. 4c also shows a retraction cable 46 may be used to operate the catch mechanism 44 which could be pivotally connected at one end. With reference to FIG. 4a, when the surgical tool 32 is deployed from the catheter 36 it pivots on a pivot pin 48 which extends through the stabilizer base 50. The surgical tool 32 may be returned to its "retracted position" from the "deployed position" shown in FIG. 4a using a mechanically controlled retraction cable 52.

FIG. 4b shows a cut away end view where the stabilizer base 50 is positioned within the catheter 36 by the pivot pin 48. For exemplary purposes, the surgical tool 32 is shown as having cutting edges 52 (which may be metallic, ceramic, polymeric, or any other suitable material) formed on the multilayered magnetoelectric portion of the surgical tool 32 (a single piezoelectric layer 54 and a single magnetostrictive layer 56 are shown for exemplary purposes).

Figure 5:
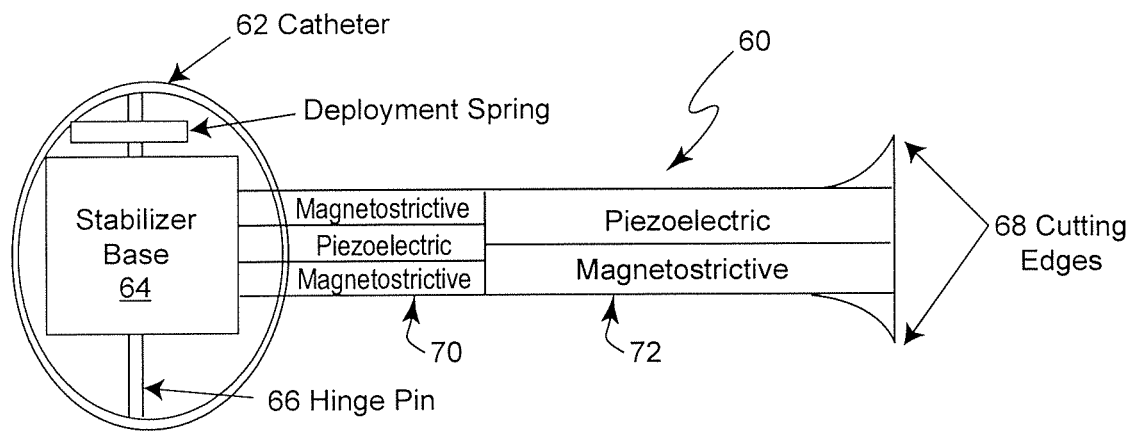
FIG. 5 shows a schematic of an exemplary cutting or scraping device which can extend and bend under an applied magnetic field.

FIG. 5 shows an embodiment of a cutting tool 60 which can extend from a catheter 62. Similar to FIGS. 4a-c, the cutting tool 60 can be pivotally connected to a stabilizer base 64 by hinge pin 66, and may have cutting edges 68 formed on its projecting end. In the configuration shown in FIG. 5, the cutting tool 60 has a first magnetoelectric portion 70 configured for elongation (this portion 70 being shown for exemplary purposes as having a piezoelectric layer sandwiched between magnetostrictive layers) and a second magnetoelectric portion 72 configured for bending (this portion 72 being shown for exemplary purposes as having a piezoelectric layer joined with a magnetostrictive layer). An applied magnetic field will cause the first portion 70 to elongate and the second portion 72 to bend. Further, the piezoelectric layer(s) in the first portion can provide feedback on the amount of actual elongation and the piezoelectric layer(s) in the second portion can provide feedback on the amount of actual bending of the second portion.

Figure 6:
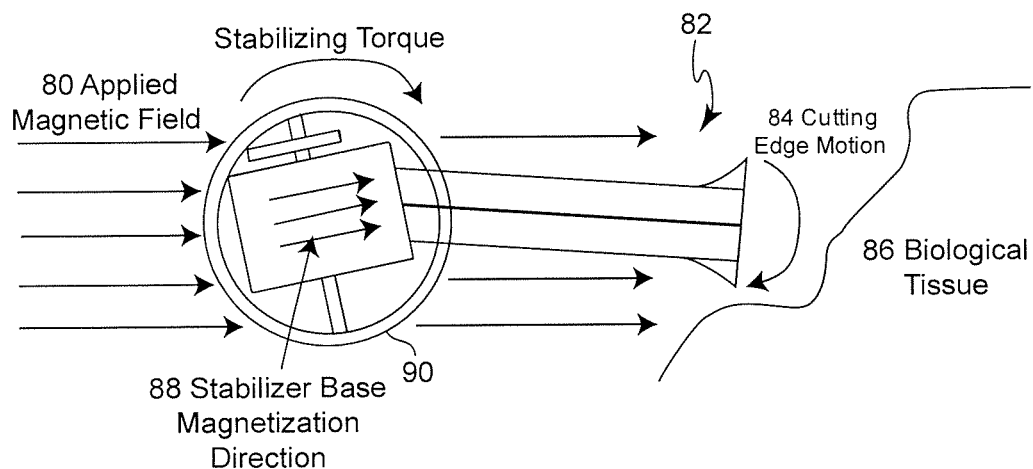
FIG. 6 shows a schematic of an exemplary cutting or scraping device which highlights stabilization at the base.

FIG. 6 shows an application where an applied magnetic field 80 is used to bend (not shown) a cutting tool 82 to achieve a cutting motion 84 in a manner which allows cutting or scraping biological tissue 86 (e.g., removing restenosis from an artery wall). This type of motion 84 can be used to cut or scrape tissue, or could be used to actuate other devices, etc. Feedback from the piezoelectric layer in the cutting tool 82 can be provided to the surgeon to let him or her know how difficult (or easy) the biological tissue is deforming or being removed. For example, if the actual amount of bending of the cutting tool 82 is approximately equal to the theoretical amount of bending which would be achieved using the applied magnetic field 80, then it can be inferred that the biological tissue 86 is either removed or is being easily removed. Conversely, if the actual amount of bending of the cutting tool as determined from output of the piezoelectric layer is significantly different from the theoretical amount of bending which would be produced by the applied magnetic field 80, it can be inferred that the biological tissue 86 is difficult to cut or scrape and that a higher applied magnetic field may be required, a pulsing of the applied magnetic field may be required, and/or some other corrective action may be required to remove the biological tissue 86. This type of feedback has heretofore not been available to a surgeon.

The embodiment shown in FIG. 6 also highlights the operability of the stabilizer base 88 within the catheter 90. In short, the stabilizer base 88 should be made of a magnetic material, a magnetizable material, or include a selectively magnetic portion (e.g., an electromagnetic coil). The stabilizer base 88, due to its magnetic poling and by a stabilizing torsional movement will assume a position in line with the applied by magnetic field 80. In this way, the surgeon can be assured that the bending of the surgical tool 82 occurs at the correct location and that the feedback measurements sensed from its piezoelectric layer are accurate.

Figure 7:
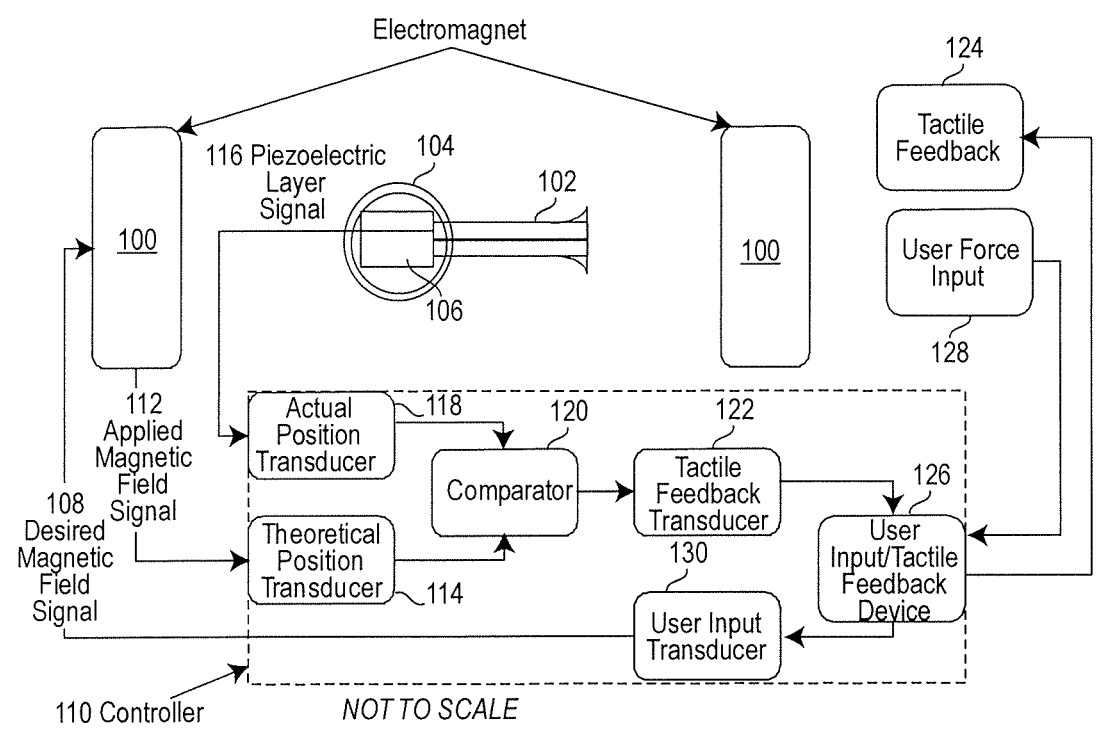
FIG. 7 shows a block diagram of an exemplary cutting or scraping device which highlights feedback control of the device.

FIG. 7 shows a block diagram illustrating a portion of the control features provided by the invention. Experiments have been conducted using laser measurements of a cantilevered member that includes at least one magnetostrictive layer and at least one piezoelectric layer. The experiments demonstrated that the cantilevered member can be caused to bend an amount equivalent to a theoretical amount (i.e., actual=theoretical) under the influence of an applied magnetic field. That is, the bending which would be predicted based on the attributes of the cantilevered member and the applied magnetic field was actually achieved as confirmed using laser measurement techniques. Furthermore, these experiments provided for sensing of the magnetoelectric element based on output of the one or more piezoelectric layers. The sensed amount of bending determined from the piezoelectric layer(s) corresponded with the laser determined measurements. Thus, this establishes that the electric output from a bending or elongating piezoelectric layer in a multilayer magnetoelectric element can provide accurate measurements of the actual bending or elongation of the magnetoelectric element. The inventor has recognized that the piezoelectric layer(s) can thus provide an accurate feedback mechanism which a surgeon might use in assessing the performance of a deployed cutting or scraping (or other tool) under the influence of an applied magnetic field, and that this information can be provided to the surgeon to provide for feedback that he or she might use during a surgical procedure. Currently, this type of feedback is not provided to a surgeon, thus, when a surgeon is using a computer controlled tool, he or she might be handicapped by the fact that they cannot "feel" what is occurring in the tissues which are being acted upon the way they can for other surgical procedures.

With reference to FIG. 7, it can be seen that a magnetic field generated by magnets 100 can be used to controllably operate on (e.g., bend or elongate or both) a surgical tool 102 which includes one or more piezoelectric layers and one or more magnetostrictive layers. The surgical tool 102 may be selectively deployed from an opening in a catheter 104 and may be secured to a magnetized stabilizing base 106 as discussed in more detail above.

A controller 110 is used to control the magnetic field by sending signals 108 that are designed to achieve a certain applied magnetic field in a subject positioned between the magnets 100. The controller 110 receives applied magnetic field signals 112 from the magnets 100 (or device associated therewith) From the field signals 112, the controller 110 can compute a theoretical position of the surgical cutting tool. This computation is shown generically as theoretical position transducer 114; however, it should be recognized that this can be accomplished using a computer internally or externally to the controller 110.

A signal 116 from the piezoelectric layer is input to the controller 110, and from signal 116, the actual position of the cutting tool 102 can be determined. This computation is shown generically as actual position transducer 118; however, it should be recognized that this can be accomplished using a computer internally or externally to the controller 110.

A comparator 120 is used to compare the actual position of the cutting tool 102 sensed using the piezoelectric layer in the magnetoelectric element with the theoretical position of the cutting tool 102 computed from the applied magnetic field and with a description of the physical attributes of the cutting tool 102. From this comparison, a difference signal can be used to generate a signal for feedback to the surgeon. This is shown generically as tactile feedback transducer 122; however, it should be understood that the feedback transducer 122 could be used to send a signal to an external display for a surgeon to see the difference signal in terms of an image, graph, or table, as well as could be sent to a device 124 which provides tactile feedback such as for example mechanical pressure exerted on an operating handle (e.g., inflation of a balloon member, movement of a geared member or levered member, drag on a joystick type device, etc.) Thus, the tactile feedback device 124 can be a device which provides actual tactile feedback that can be felt by the surgeon or feedback on a display that can be viewed by the surgeon or both.

The controller 110 has an interface 126 which allows for providing tactile feedback signals to the tactile feedback device 126. The interface 126 also allows the user to input control signals to a user force input device 128. For example, if a force-feedback joystick is used, the joystick may drag or slow a response as tactile feedback to the user (tactile feedback 124) when there are large differences between the actual and theoretical positions of the cutting tool (i.e., the amount of bending or the amount of extending which is actually measured is different from that which should be theoretically achieved using the applied magnetic field 112). The surgeon might then move the joystick (an exemplary input device 128) forward (or push a button harder, etc.) to tell the controller 110 that more power or less power or a pulsing amount of power should be applied to the magnets 100. The signals directed from the input device 128 are received at the interface and translated to control signals for causing desired magnetic field signals 108 to be delivered to the magnets 100. This is shown generically as user input transducer 130; however, it should be understood that this function can be achieved internally or externally to the controller 110. Similarly, if the joystick or other tactile feedback 124/user force input device 128 (i.e., a joystick can perform both functions in one device—other configurations with two separate devices can also be used in the practice of the invention) is providing feedback that suggests that the actual position and theoretical position of the cutting tool are about the same, the surgeon will know that a procedure could be stopped (e.g., this might signal that most of a plaque is removed, or it might signal that most of the cutting required has been performed for achieving a specific result, etc.)

Figure 8:
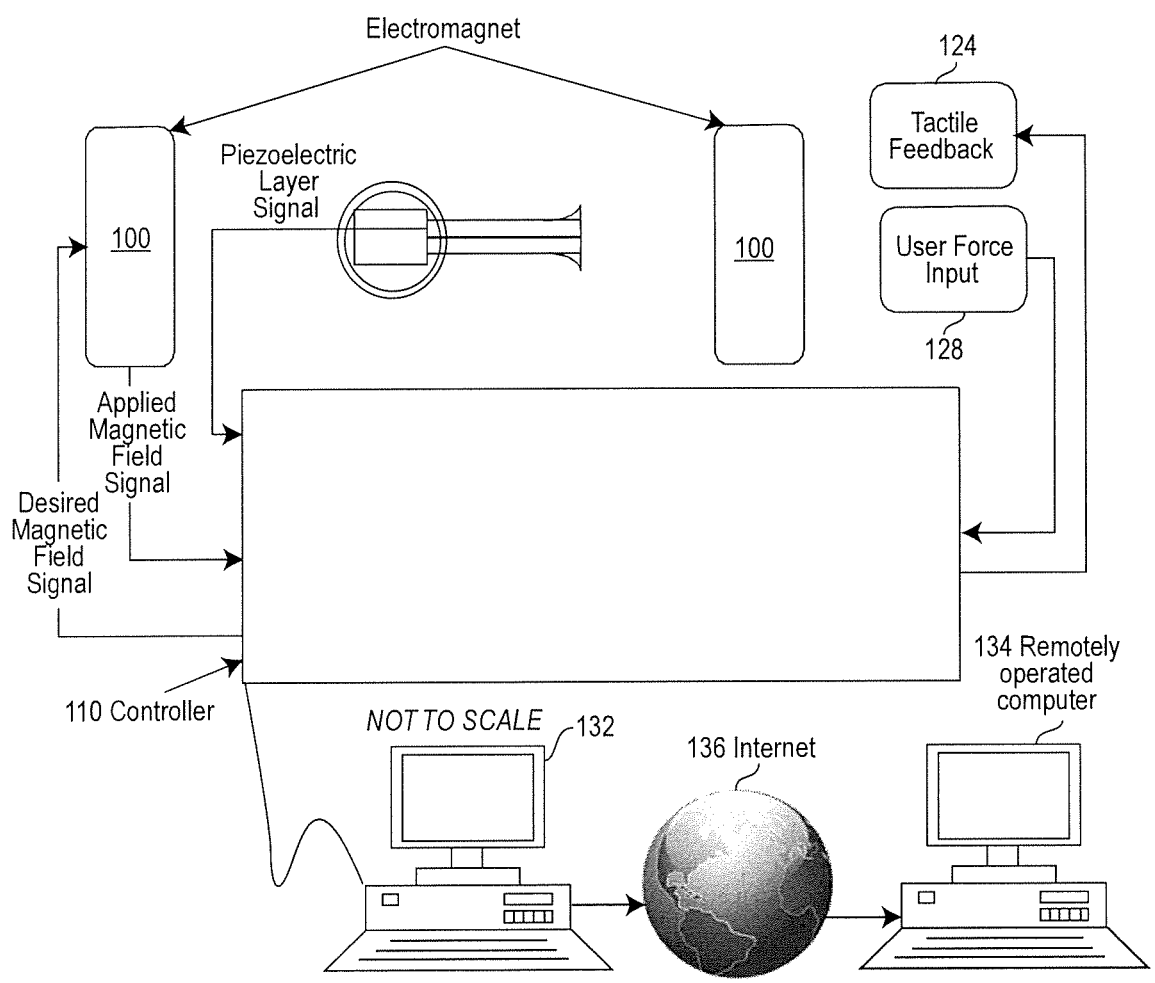
FIG. 8 is a block diagram similar to FIG. 7, but which shows remote control operation, such as over the Internet.

FIG. 8 shows the same block diagram as in FIG. 7 with the added feature that a computer 132 (or other interface) connects the controller 110 to a remote computer 134 through a network such as the internet 136 (or other network, e.g., WLAN, etc.) This allows a surgeon to remotely perform the surgery on a subject. The tactile feedback 124/user force input (such as a joystick) can be connected directly to the remote computer 134 for allowing the surgeon to be provided with tactile feedback at his hand (as well as visual feedback on the computer display.

Figure 9:
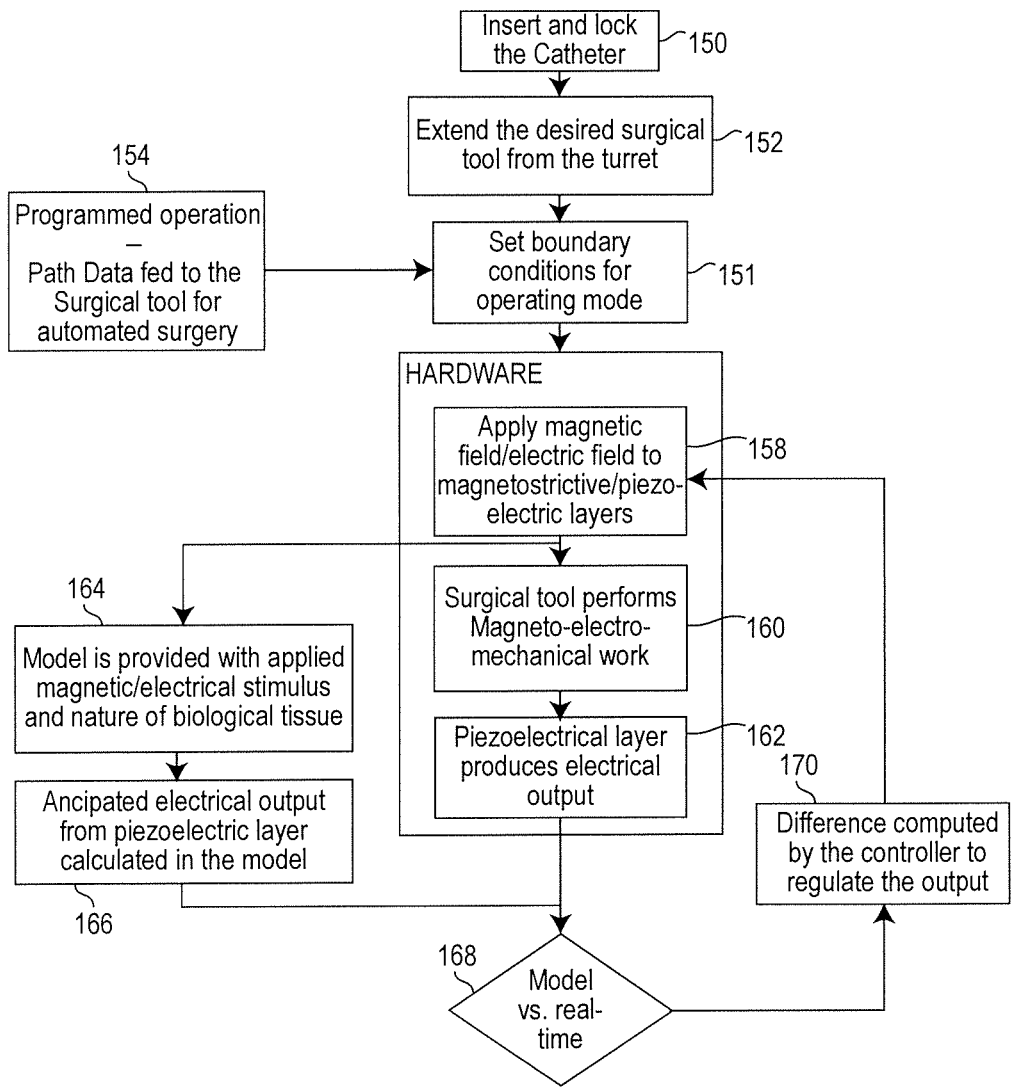
FIG. 9 is a flow diagram illustrating an example of a feedback control which is achieved with an exemplary cutting or scraping device.

FIG. 9 shows a high level flow diagram of how the surgical tool and system may operate (it being understood that many permutations and additions to this basic flow strategy could be practiced within the scope of the invention). At step 150 the catheter is inserted into the subject and locked. At step 152, the surgical tool is extended from a turret. This extension will generally occur at the cite where a surgical procedure is to be performed, such as plaque removal, etc. Steps 154 and 156 contemplate providing programmed operation information and setting boundary conditions for the operating mode. Steps for the Hardware as shown in FIG. 7 above are performed at 158, 160, and 162. At step 158, the magnetic field is applied to magnetoelectric element by magnets positioned external to the subject. At step 160, the mechanical work is performed by the surgical tool with the magnetoelectric portion (e.g., the scraping, cutting, etc.) (real time values of tip displacement, velocity, etc. can be sensed). At step, 162, electric output from the piezoelectric layer of the magnetoelectric component is directed to the controller. The electrical output is indicative of the "actual" position of the tool (e.g., degree of bending, amount of extension, etc.). Simultaneously, at steps 164 and 166, the "theoretical" amount of bending or extension is determined by providing the magnetic field input information, the characteristics of the tool, and the nature of the biological tissue information. From this the anticipated electrical output from the piezoelectric layer can be calculated. At comparison block 168, the calculated output for the piezoelectric layer (step 166) for a theoretical amount of bending or extension is compared with the "actual" output produced by the piezoelectric layer (step 162) in the magnetoelectric structure. The difference is computed at step 170, and this can provide tactile and visual feedback to the surgeon so that he or she can regulate the applied magnetic field in a desired fashion.

While the above description contemplates an active device where the magnetic field is used to cause a scraping or cutting action, it will be recognized that the magnetoelectric element might be used as a sensor. For example, the magnetoelectric element could be extended or bent under the influence of an applied magnetic field and be brought into contact with a plaque. The extended tool could then be "rubbed" against the plaque by surgeon-controlled input adjustments to the magnetic field. As the extended tool is "rubbed" against the plaque, its actual position will deflect more or less from the theoretical position computed from the applied magnetic field, and this difference is sensed using the piezoelectric layer(s) as discussed above. From this difference the feedback to the surgeon may help him or her deduce the amount of plaque present. This might also be used as a technique for deducing different types of tissues, etc. which are encountered by an extended tool.

Figure 10C:
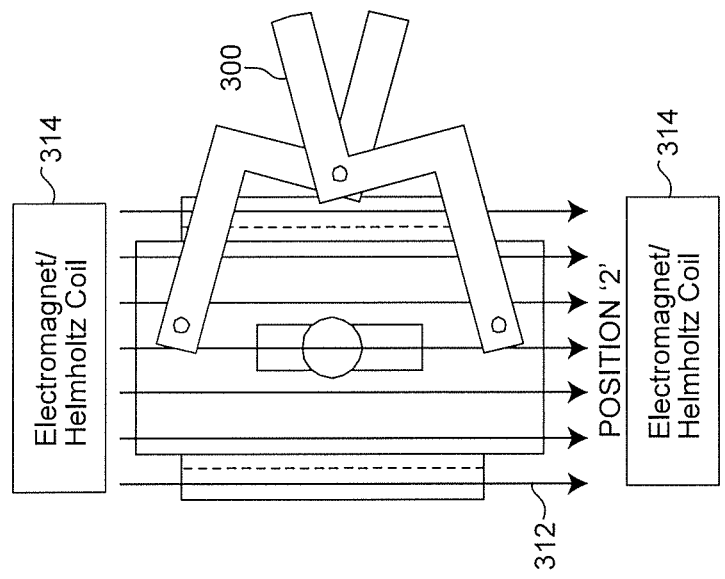
FIGS. 10a-c are schematic diagrams of an exemplary cutting device.
Figure 10A:
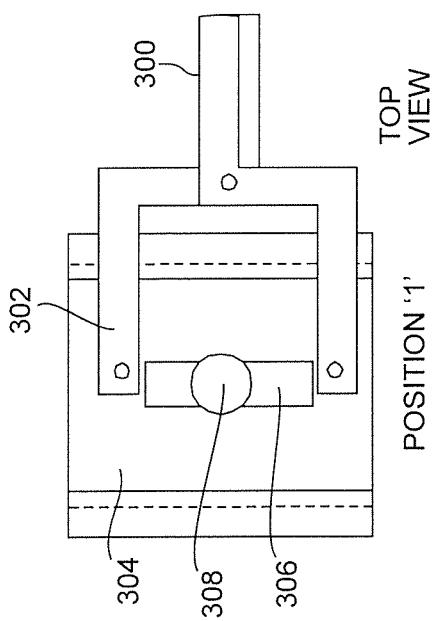
Figure 10B:
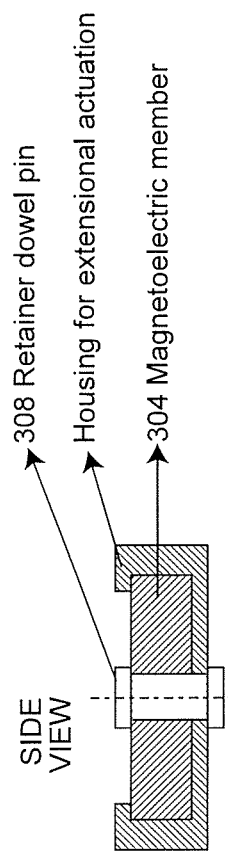

While the above description primarily contemplates bending activity by the magnetoelectric element (as discussed in conjunction with FIG. 1a), it will be recognized that there are a variety of applications where only extension of the magnetoelectric layer is required. For example, FIGS. 10a-c shows an example of a compact micro-scale (300-500 microns) cutting tool 300. With reference to FIG. 10a, the cutting tool 300 is in a closed position. Ends 302 of the cutting tool 300 are affixed to a magnetoelectric element 304. The magnetoelectric element 304 preferably has an opening 306 though which a guide rod or retainer dowel pin 308 extends. FIG. 10b shows that the housing 310 can hold the magnetoelectric element 304. Together, the pin 308 and opening 306 and housing 310, can be used to assure that the magnetoelectric element 304 is held in a way which allows for longitudinal expansion in an applied magnetic field. FIG. 10c shows that when a magnetic field 312 is applied by Helmholtz coils or other magnetic 314 devices, the cutting tool 302 can be caused to move to an open position for cutting tissue within the subject. Thus be manipulating the magnetic field 312, the cutting tool 300 can open and close to cut tissues of interest. Differences in the properties of the tissues being cut can cause the "actual" and "theoretical" position of the elongated magnetoelectric element 304 to differ. These differences can be used to provide feedback (tactile, visual, or both) to a surgeon so that he or she can cause the controller to adjust the magnetic field 332 in a manner which achieves a desired result. The surgeon would also be able to more easily identify when the tissue to be cut has been cut through because at that moment the "actual" and "theoretical" positions of the magnetoelectric tool would be about the same. In this manner the surgeon would be able to know when to apply more magnetic field, pulse the field, or stop applying the field so that he or she could more precisely control the cutting action of the cutting tool.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A surgical tool, comprising:
    a magnetoelectric member attached to a catheter, wherein the magnetoelectric member includes at least one piezoelectric layer and at least one magnetostrictive layer, wherein said magnetoelectric member is configured to be inserted and deployed into a subject and is operable inside said subject to one or more of bend or elongate based on an applied magnetic field applied externally to said subject, wherein said at least one piezoelectric layer produces an electrical output;
    a controller configured to determine a difference between an actual amount of bending or elongation of said magnetoelectric member based on said electrical output from said at least one piezoelectric layer and a theoretical amount of bending or elongation of said magnetoelectric member based on said applied magnetic field; and
    a feedback member configured to provide feedback to a user of said surgical tool based on an amount of said difference determined by said controller.

2. The surgical tool of claim 1 further comprising a magnetized stabilizer connected to said magnetoelectric member which stabilizes said magnetoelectric member in said applied magnetic field.

3. The surgical tool of claim 1, wherein said feedback member includes a display for displaying one or more of an image, graph, or table which provides an indication of said difference determined by said controller.

4. The surgical tool of claim 1, wherein said feedback member provides tactile feedback based on said difference determined by said controller.

5. The surgical tool of claim 1, wherein said at least one magnetostrictive layer is selected from the group consisting of Galfenol (Iron Gallium), Terfenol-D (Terbium Dysprosium Iron), Cobalt Ferrite, Nickel Ferrite, Lithium Ferrite, Yttrium Iron Garnet, Copper Ferrite, Manganese Ferrite, $LaCaMnO_3$, $LaSrMnO_3$, $SmFe_2$, $TbFe_2$, Permendur (Iron Cobalt Vanadium), $Ni2MnGa$, Nickel, and Metglas.

6. The surgical tool of claim 1, wherein said at least one piezoelectric layer is selected from the group consisting of Lead Zirconate Titanate, Lead Magnesium Niobate-Lead Titanate, Polyvinylidine Fluoride, and Lead Zirconium Niobate-Lead Titanate.

7. A system for surgical operations, comprising:
  a magnetic field generating device for generating an applied magnetic field external to a subject, wherein at least a portion of said applied magnetic field is capable of permeating said subject; and
  a surgical tool comprising:
    a magnetoelectric member attached to a catheter, wherein the magnetoelectric member includes at least one piezoelectric layer and at least one magnetostrictive layer, wherein said magnetoelectric member is configured to be inserted and deployed into a subject and is operable inside said subject to one or more of bend or elongate based on an applied magnetic field applied externally to said subject, wherein said at least one piezoelectric layer produces an electrical output;
    a controller configured to determine a difference between an actual amount of bending or elongation of said magnetoelectric member based on said electrical output from said at least one piezoelectric layer and a theoretical amount of bending or elongation of said magnetoelectric member based on said applied magnetic field; and
    a feedback member configured to provide feedback to a user of said surgical tool based on an amount of said difference determined by said controller.

8. The system of claim 7, wherein said feedback member includes a display for displaying one or more of an image, graph, or table which provides an indication of said difference determined by said controller.

9. The system of claim 7, wherein said feedback member provides tactile feedback based on said difference determined by said controller.

10. The system of claim 7 wherein said magnetic field generating device includes at least one electromagnet.

11. A surgical tool, comprising:
  a magnetoelectric member including at least one piezoelectric layer and at least one magnetostrictive layer, wherein said magnetoelectric member is attached to a catheter, is configured to be inserted and deployed into a subject, undergoes elongation and bending due to an applied magnetic field applied externally to said subject, and is configured to perform surgical procedures;
  a comparator configured to determine a difference between an actual elongation or bending of said magnetoelectric member and a theoretical elongation or bending of said magnetoelectric member for said applied magnetic field based on an electrical output from said at least one piezoelectric layer connected by a wire or by wireless communication with said comparator;
  a controller incorporating said comparator, said controller configured to generate an electrical signal indicative of said difference;
  an input device connected to said controller operated by a user, said input device configured to adjust said applied magnetic field and to provide a tactile feedback to said user through said input device based on said electrical signal generated by said controller; and
  a computer connected to said input device, said computer configured to adjust said applied magnetic field to remotely perform said surgical procedures inside said subject based on said electrical signal generated by said controller.

* * * * *